United States Patent [19]

Waranis et al.

[11] Patent Number: 5,616,588
[45] Date of Patent: Apr. 1, 1997

[54] RAPAMYCIN FORMULATION FOR IV INJECTION

[75] Inventors: Robert P. Waranis, Chazy, N.Y.; Thomas W. Leonard, Wilmington, N.C.

[73] Assignee: American Home Products Corporation, Madison, N.J.

[21] Appl. No.: 302,190

[22] Filed: Sep. 12, 1994

Related U.S. Application Data

[63] Continuation-in-part of Ser. No. 129,526, Sep. 30, 1993, abandoned.
[51] Int. Cl.$^6$ .................................................... A61K 31/44
[52] U.S. Cl. ............................................................ 514/291
[58] Field of Search ............................................. 514/291

[56] References Cited

U.S. PATENT DOCUMENTS

| | | | |
|---|---|---|---|
| 3,929,992 | 12/1975 | Sehgal et al. | 514/291 |
| 3,993,749 | 11/1976 | Sehgal et al. | 514/291 |
| 4,885,171 | 12/1989 | Surendra et al. | 514/291 |
| 5,080,899 | 1/1992 | Sturm et al. | 514/291 |
| 5,100,899 | 3/1992 | Caln | 514/291 |

FOREIGN PATENT DOCUMENTS

| | | | |
|---|---|---|---|
| 0041795 | 12/1981 | European Pat. Off. | 514/291 |
| 0428162 | 5/1991 | European Pat. Off. . | |
| 0444659 | 9/1991 | European Pat. Off. . | |
| 921437 | 9/1992 | WIPO . | |

OTHER PUBLICATIONS

Physicians' Desk Reference, 45th ed., 1991, pp. 2119–2122, Medical Economics Company, Inc.

Physicians' Desk Reference, 45th ed., 1991, pp. 785–787, Medical Economics Company, Inc.

Luke et al., Effects of Cyclosporine on the Isolated Perfused Rat Kidney, Transplantation, vol. 43, No. 6, pp. 795–799, 1987.

Venkataram, et al., Pharmacokinetics of Two Alternative Dosage Forms for Cyclosporine: Liposomes and Intralipid, Journal of Pharmaceutical Sciences, vol. 79, No. 3, pp. 216–219, 1990.

Thiel, et al., Acutely Impaired Renal Function During Intravenous Administration of Cyclosporine A: A Cremaphore Side–Effect, Clinical Nephrology, vol. 25, Suppl. No. 1., pp. S40–S42, 1986.

Honbo, et al., The Oral Dosage Form of FK–506, Transplantation Proceedings, vol. XIX, No. 5, Suppl. 6, pp. 17–22, 1987.

Stepkowski, et al., Rapamycin, A Potent Immunosuppressive Drug for Vascularized Heart, Kidney, and Small Bowel Transplantation in the Rat, Transplantation, vol. 51, No. 1, pp. 22–24, 1991.

Kahan, et al., Synergistic Interactions of Cyclosporine and Rapamycin to Inhibit Immune Performances of Normal Human Peripheral Blood Lymphocytes In Vitro, Transplantation, vol. 51, No. 1, pp. 232–237, 1991.

Intl. Pharm. Abstracts—FK–506, Immunosuppressant for the 1990s, Macleod, et al., Lancet, 337, pp. 25–27, Jan. 5, 1991.

Intl. Pharm. Abstracts, FK–506: Discussion of a New Investigationsl Drug, C.G. Forde, ASHP Midyear Clinical Meeting, 25, p. 446D, Dec. 1990.

Intl. Pharm. Abstracts, FK–506, Kidney Transplantation Under FK 506, Starzl, et al., JAMA, 264, pp. 63–67, Jul. 4, 1990.

Intl. Pharm. Abstracts—FK–506 In Steroid–Resistant Focal Sclerosing Glomerulonephritis of Childhood, McCauley, et al., Lancet, 335, p. 674, Mar. 17, 1990.

Intl. Pharm. Abstracts, New Drug Could Replace Cyclosporin in Transplant Drug Therapy, Anon, Am. Pharm. NS, 30, 16, Jan. 1990.

Intl. Pharm. Abstracts, Treatment of Cyclosporin Induced Hemolytic–Uremic Syndrome with FK–506, McCauley, et al., Lancet, 2, 1516, Dec. 23–30, 1989.

Intl. Phar,. Abstracts—FK–506 for Liver, Kidney, and Pancreas Transplantation; Starzl, et al., Lancet, 2, 1000–1004, Oct. 28, 1989.

*Primary Examiner*—Jerome D. Goldberg
*Attorney, Agent, or Firm*—Arthur G. Seifert

[57] ABSTRACT

Disclosed herein is an aqueous, injectable rapamycin solution comprising 40 to 75 volume percent of a concentrate solution of rapamycin in propylene glycol, at concentrations of rapamycin ranging from 0.25 mg/ml to 8 mg/ml, in combination with a diluent solution comprising water, wherein the diluent comprises 60 to 25 volume percent of the combined solution and the concentration of rapamycin in the combined solution ranges from 0.1 mg/ml to 4 mg/ml.

15 Claims, No Drawings

RAPAMYCIN FORMULATION FOR IV INJECTION

This application is a continuation-in-part of U.S. patent application Ser. No. 08/129,526, filed on Sep. 30, 1993, now abandoned.

This invention relates to a rapamycin formulations for iv injection. The invention disclosed herein provides an aqueous formulation of rapamycin for intravenous injection (iv) without the need of a surfactant. In one aspect the invention comprises a concentrate solution of rapamycin in propylene glycol, in combination with a diluent consisting of water, in given proportions as described below.

Rapamycin is a macrolide antibiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin is insoluble in water and is only slightly soluble in solubilizers, such as propylene glycol, glycerin and PEG 400, commonly used in preparing parenteral formulations. It is only sparingly soluble in PEG 300 and is insoluble or very slightly soluble in commonly used aqueous injectable co-solvent systems, such as, 20% ethanol/water, 10% DMA/water, 20% Cremophor EL®/water and 20% polysorbate 80/water. For these reasons clinically and commercially acceptable injectable formulations of rapamycin have been difficult to make. An injectable composition of rapamycin is described in European Patent Publication No. 0041795, published Dec. 16, 1981. In this injectable formulation rapamycin is first dissolved in a low boiling point organic solvent, namely, acetone, methanol or ethanol. This solution is then mixed with a nonionic surfactant selected from polyoxyethylated fatty acids; polyoxyethylated fatty alcohols; and polyoxyethylated glycerin hydroxy fatty acid esters, e.g. polyoxyethylated castor oil, exemplified by Cremophor® EL and polyoxyethylated hydrogenated castor oil, exemplified by Cremophor® RH 40 and Cremophor® RH 60. Cremophor® EL is the primary nonionic surfactant used in the examples.

The primary immunosuppressive agent presently used for inhibiting rejection in the allograft transplantation of organs in man is cyclosporine (Sandimmune®). Cyclospofine is a cyclic polypeptide consisting of 11 amino acids. The intravenous injectable formulation of Sandimmune® (IV) is a sterile ampul containing, per ml, 50 mg of cyclospofine, 650 mg of Cremophor® EL and alcohol Ph Helv. (32.9% by volume) (under nitrogen). For administration this mixture is diluted further with 0.9% Sodium Chloride Injection or 5% Dextrose Injection before use. (*Physicians' Desk Reference*, 45th ed., 1991, pp. 1962–64, Medical Economics Company, Inc.) The macrolide molecule designated FK506, which has certain structural similarities to rapamycin, is also currently undergoing clinical investigation for inhibiting rejection in allograft organ transplantation in man. FK506 is isolated from *Streptomyces tsuskubaensis* and is described in U.S. Pat. No. 4,894,366 to Okuhara et al., issued Jan. 16, 1990 R. Venkataramanan et al., in Transplantation Proceedings, 22, No. 1, Suppl., 1 pp 52–56 (February 1990), report that the intravenous injectable formulation of FK506 is provided as a 10 mg/ml solution of FK506 in polyoxyethylated castor oil (HCO-60, a surfactant) and alcohol. The intravenous preparation must be diluted with saline or dextrose and administered as an infusion for 1 to 2 hours.

Applicants have now surprisingly found that a pharmaceutically acceptable aqueous, injectable solution of rapamycin may be obtained without the use of a surfactant by using propylene glycol to solubilize rapamycin in a two part system of rapamycin concentrate and water diluent. A particular advantage of this is the use of water as a one component diluent which is preferred for injectable solutions for tissue tolerance. Additionally, mixing of other diluent ingredients is avoided. The injectable rapamycin formulations of the invention are well suited to both bolus injection and infusion.

One aspect of this invention is an aqueous-based, injectable rapamycin solution comprising a concentrate solution of rapamycin in propylene glycol in combination with a diluent solution comprising water. Specifically, Applicants' invention is an aqueous, injectable rapamycin solution comprising 40 to 75 volume percent of a concentrate solution of rapamycin in propylene glycol, at concentrations of rapamycin ranging from 0.25 mg/ml to 8 mg/ml, in combination with a diluent solution comprising water, wherein the diluent comprises 60 to 25 volume percent of the combined solution and the concentration of rapamycin in the combined solution ranges from 0.1 mg/ml to 4 mg/ml. Preferred aqueous, injectable rapamycin solutions are those wherein the diluent solution is 40 to 60 volume percent of the combined solution. The diluent is preferably water but may also comprise other solvents such as propylene glycol in small amounts eg 10% by volume or less.

Preferred aqueous, injectable rapamycin solutions of this aspect of the invention are those in which the concentration of rapamycin in the propylene glycol concentrate ranges from 0.5 mg/ml to 4 mg/ml. More preferred are those in which the concentration of rapamycin in the propylene glycol concentrate ranges from 0.6 mg/ml to 3.3 mg/ml. Also preferred aqueous, injectable rapamycin solutions of the invention are those in which the concentration of rapamycin in the combination solution ranges from 0.25 mg/ml to 2 mg/ml and those wherein the propylene glycol comprises 60 to 40 volume percent of the combined solution.

Especially preferred aqueous, injectable rapamycin solutions according to this aspect of the invention comprise 40 to 60 percent of a concentrate solution of rapamycin in propylene glycol, at concentrations of rapamycin ranging from 0.5 mg/ml to 4 mg/ml, in combination with a 60 to 40 volume percent diluent comprising water, wherein the concentration of rapamycin in the combined solution ranges from 0.25 mg/ml to 2 mg/ml.

This invention also provides an aqueous, injectable rapamycin solution as described above for bolus injection, wherein the concentration of rapamycin in the injectable solution preferably ranges from 0.25 mg/ml to 2 mg/ml.

A second aspect of this invention is an aqueous, injectable solution of rapamycin, said solution comprising rapamycin in a solution of propylene glycol, and water, wherein water comprises 40 to 75 volume percent of the solution and the concentration of rapamycin in the solution ranges from 0.1 mg/ml to 4 mg/ml.
}

Preferred aqueous, injectable rapamycin solutions of this aspect of the invention are those wherein the concentration of rapamycin in the solution ranges from 0.25 mg/ml to 1 mg/ml. Also preferred, independently, are those wherein the water comprises 60 to 40 volume percent of the solution.

This invention further provides a product containing a concentrate solution of rapamycin and a diluent, as a combined preparation for mixing prior to IV injection to give a solution having a concentration of rapamycin in the range 0.1 mg/ml to 4 mg/ml; said concentrate solution comprising rapamycin in propylene glycol in the range 0.25 mg/ml to 8 mg/ml; said diluent solution comprising water, the ratio of concentrate to diluent being in the range from 40:60 to 75:25 volume percent.

The manufacture of rapamycin iv concentrate comprises adding the rapamycin to the propylene glycol and mixing until a solution results, which may be accomplished at room temperatures. The solution is then filtered in a known manner for sterility. Appropriate volumes of the concentrate solution are filled into ampules which are then sealed in a known manner. In accordance with standard manufacturing procedures for injectables, sterile conditions are maintained throughout the filtering, filling and sealing operations. The product rapamycin concentrate is best stored under refrigeration.

The manufacture of each of the rapamycin iv diluent systems comprises filling vials with appropriate volumes of sterile water, after which the vials are stoppered, sealed and autoclaved. The completed rapamycin diluent solution may be stored at room temperature or under refrigeration.

The procedure for constituting the final formulas for administration comprises injecting an aliquot of rapamycin iv concentrate into a vial containing the rapamycin iv diluent, shaking for approximately one minute or until a clear solution results. The constituted solution should be administered within the stated use period. The use period of constituted rapamycin injectable solutions is the period of time during which the constituted solution remains clear and colorless. The use period may range up to 4 hours, but a use period of up to 1 hour is preferred. Propylene glycol for pharmaceutical use is readily obtained from various commercial sources.

Accordingly this invention also provides a process for preparing an aqueous, injectable rapamycin solution which comprises mixing 40 to 75 volume percent of a concentrate solution of rapamycin in propylene glycol, at concentrations of rapamycin ranging from 0.25 mg/ml to 8 mg/ml, with a diluent solution comprising water, wherein the diluent comprises 60 to 25 volume percent of the combined solution; such that the concentration of rapamycin in the injectable solution ranges from 0.1 mg/ml to 4 mg/ml.

The following examples further illustrate the practice of the invention.

Example 1
Preparation of Rapamycin Injectable Formulation (1 mg/ml)

A. Preparation of Rapamycin IV Concentrate at 2 mg/ml in Propylene Glycol Formula (Density - 1.036 g/ml):

| Ingredients | | Amount |
| --- | --- | --- |
| Rapamycin @ 100% | | 0.2 gm |
| Propylene Glycol, USP | qs | 100 ml or 103.6 gm |

Procedure:

1. Weigh the rapamycin into a suitably calibrated container.
2. Adjust volume to 100 ml with Propylene Glycol.

Example 1
Preparation of Rapamycin Injectable Formulation (1 mg/ml)

3. Mix until a uniform solution results.
4. Sterile filter the solution.
5. Package into ampules or vials and seal.

B. Diluent for Rapamycin IV at 1.0 mg/ml

Formula (Density - 1.00 gm/ml):

| Ingedients | | Amount |
| --- | --- | --- |
| Water for Injection, USP | qs | 100 ml or 100 gm |

Procedure:

1. Fill 1.0 ml ± 0.01 ml into each 5 ml flint vial, seal and crimp.
2. Autoclave to achieve sterility.

C. Rapamycin IV solution at 1 mg/ml (constituted)
Formula (Density - 1.035 gm/ml):

| Ingredients | Amount |
| --- | --- |
| Rapamycin IV Concentrate @ 2 mg/ml | 1 ml |
| Diluent for IV-rapamycin | 1 ml |

Procedure:

1. Inject 1 ml of Rapamycin IV Concentrate at 2 mg/ml into a vial containing 1 ml of diluent for IV-rapamycin using good sterile technique.
2. Shake until a clear solution results.
3. Administer within use period.

Example 2
Preparation of Rapamycin Injectable Formulation (2 mg/ml)

A. Preparation of Rapamycin IV Concentrate at 4 mg/ml in Propylene Glycol Formula (Density - 1.036 g/ml):

| Ingredients | | Amount |
| --- | --- | --- |
| Rapamycin @ 100% | | 0.4 gm |
| Propylene Glycol, USP | qs | 100 ml or 103.6 gm |

Procedure:

1. Weigh the rapamycin into a suitably calibrated container.
2. Adjust volume to 100 ml with Propylene Glycol.
3. Mix until a uniform solution results.
4. Sterile filter the solution.
5. Package into ampules or vials and seal.

B. Diluent for Rapamycin IV at 2 mg/ml

| Ingredients | | Amount |
| --- | --- | --- |
| Propylene Glycol, USP | | 10 ml |
| Water for Injection, USP | qs | 100 ml |

Procedure:

1. Place the propylene glycol into a suitable container.
2. Adjust volume to 100 ml with Water for Injection.
3. Mix until a uniform solution results.
4. Sterile filter the solution.
5. Package.
6. Autoclave to achieve sterility.

C. Rapamycin IV solution at 4 mg/ml (constituted)
Formula (Density - 1.035 gm/ml):

| Ingredients | Amount |
| --- | --- |
| Rapamycin IV Concentrate @ 4 mg/ml | 1 ml |
| Diluent for IV-rapamycin | 1 ml |

Procedure:

1. Inject 1 ml of Rapamycin IV Concentrate at 2 mg/ml into a vial containing 1 ml of diluent for IV-rapamycin using good sterile technique.
2. Shake until a clear solution results.
3. Administer within use period.

Example 3
Preparation of Rapamycin Injectable Formulation (3 mg/ml)

A. Preparation of Rapamycin IV Concentrate at 6 mg/ml in Propylene Glycol Formula (Density - 1.036 g/ml):

| Ingredients | Amount |
| --- | --- |
| Rapamycin @ 100% | 0.6 gm |
| Propylene Glycol, USP    qs | 100 ml or 103.6 gm |

Procedure:
1. Weigh the rapamycin into a suitably calibrated container.
2. Adjust volume to 100 ml with Propylene Glycol.
3. Mix until a uniform solution results.
4. Sterile filter the solution.
5. Package into ampules or vials and seal.

B. Diluent for Rapamycin IV at 3 mg/ml

Formula (Density - 1.00 gm/ml):

| Ingredients | Amount |
| --- | --- |
| Propylene Glycol, USP | 10 ml |
| Water for Injection, USP    qs | 100 ml or 100 gm |

Procedure:
1. Place the propylene glycol into a suitable container.
2. Adjust volume to 100 ml with Water for Injection.
3. Mix until a uniform solution results.
4. Sterile filter the solution.
5. Package.
6. Autoclave to achieve sterility.

C. Rapamycin IV solution at 3 mg/ml (constituted) Formula (Density - 1.035 gm/ml):

| Ingredients | Amount |
| --- | --- |
| Rapamycin IV Concentrate @ 6 mg/ml | 1 ml |
| Diluent for IV-rapamycin | 1 ml |

Procedure:
1. Inject 1 ml of Rapamycin IV Concentrate at 6 mg/ml into a vial containing 1 ml of diluent for IV-rapamycin using good sterile technique.
2. Shake until a clear solution results.
3. Administer within use period.

Example 4
Preparation of Rapamycin Injectable Formulation (4 mg/ml)

A. Preparation of Rapamycin IV Concentrate at 8 mg/ml in Propylene Glycol Formula (Density - 1.036 g/ml):

| Ingredients | Amount |
| --- | --- |
| Rapamycin @ 100% | 0.8 gm |
| Propylene Glycol, USP    qs | 100 ml or 103.6 gm |

Procedure:
1. Weigh the rapamycin into a suitably calibrated container.
2. Adjust volume to 100 ml with Propylene Glycol.
3. Mix until a uniform solution results.
4. Sterile filter the solution.
5. Package into ampules or vials and seal.

B. Diluent for Rapamycin IV at 4 mg/ml

| Ingredients | Amount |
| --- | --- |
| Propylene Glycol, USP | 10 ml |
| Water for Injection, USP    qs | 100 ml or 100 gm |

Procedure:
1. Place the propylene glycol into a suitable container.
2. Adjust volume to 100 ml with Water for Injection.
3. Mix until a uniform solution results.
4. Sterile filter the solution.
5. Package.
6. Autoclave to achieve sterility.

Example 4
Preparation of Rapamycin Injectable Formulation (4 mg/ml)

C. Rapamycin IV solution at 4 mg/ml (constituted) Formula (Density - 1.035 gm/ml):

| Ingredients | Amount |
| --- | --- |
| Rapamycin IV Concentrate @ 8 mg/ml | 1 ml |
| Diluent for IV-rapamycin | 1 ml |

Procedure:
1. Inject 1 ml of Rapamycin IV Concentrate at 8 mg/ml into a vial containing 1 ml of diluent for IV-rapamycin using good sterile technique.
2. Shake until a clear solution results.
3. Administer within use period.

What we claim is:

1. An aqueous, injectable rapamycin solution free of non-ionic surfactant obtained by a process consisting essentially of mixing 40 to 75 volume percent of a concentrate solution of rapamycin in propylene glycol, at concentrations of rapamycin ranging from 0.25 mg/ml to 8 mg/ml, with a diluent consisting essentially of water, wherein the diluent ranges from 60 to 25 volume percent of the combined solution; such that the concentration of rapamycin in the injectable solution ranges from 0.1 mg/ml to 4 mg/ml.

2. An aqueous, injectable rapamycin solution according to claim 1 wherein the concentrate solution of rapamycin in propylene glycol ranges from 40 to 60 volume percent of the injectable solution.

3. An aqueous, injectable rapamycin solution according to claim 1 wherein the concentration of rapamycin in the propylene glycol concentrate ranges from 0.5 mg/ml to 4 mg/ml.

4. An aqueous, injectable rapamycin solution according to claim 1 for bolus injection wherein the concentration of rapamycin in the injectable solution ranges from 0.25 mg/ml to 2 mg/ml.

5. An aqueous, injectable rapamycin solution free of non-ionic surfactant obtained by a process consisting essentially of mixing 40 to 60 volume percent of a concentrate solution of rapamycin in propylene glycol, at concentrations of rapamycin ranging from 0.5 mg/ml to 4 mg/ml, with a diluent consisting essntially of water, wherein the diluent ranges from 60 to 40 volume percent of the combined solution; such that the concentration of rapamycin in the injectable solution ranges from 0.25 mg/ml to 2 mg/ml.

6. An aqueous, injectable rapamycin solution according to claim 5 wherein the concentrate solution of rapamycin in propylene glycol ranges from 40 to 50 volume percent of the injectable solution.

7. An aqueous, injectable rapamycin solution according to claim 5 wherein the concentration of rapamycin in the propylene glycol concentrate ranges from 0.6 mg/ml to 3.3 mg/ml.

8. An aqueous, injectable rapamycin solution according to claim 5 wherein the concentration of rapamycin in the injectable solution ranges from 0.5 mg/ml to 1.5 mg/ml.

9. An aqueous, injectable rapamycin solution free of non-ionic surfactant, said injectable solution consisting essentially of rapamycin in a solution of propylene glycol and water, wherein 40 to 75 volume percent of the solution is water, and the concentration of rapamycin in the solution ranges from 0.1 mg/ml to 4 mg/ml.

10. An aqueous, injectable rapamycin solution according to claim 9 wherein 40 to 60 volume percent of the solution is water, and the concentration of rapamycin in the solution ranges from 0.25 mg/ml to 2 mg/ml.

11. A product containing a concentrate solution of rapamycin and a diluent, as a combined preparation for mixing prior to IV injection to give a solution free of non-ionic surfactant and having a concentration of rapamycin in the range 0.1 mg/ml to 4 mg/ml; said concentrate solution consisting essentially of rapamycin in propylene glycol in the range 0.25 mg/ml to 8 mg/ml; said diluent consisting essentially of water, the ratio of concentrate to diluent being in the range from 40:60 to 75:25 volume percent.

12. A product according to claim 11 wherein the ratio of concentrate to diluent is in the range 60:40 to 40:60 volume percent.

13. A product according to claim 11 wherein the concentration of rapamycin in the propylene glycol concentrate ranges from 0.5 mg/ml to 4 mg/ml.

14. A product according to claim 11 for bolus injection wherein the concentrate of rapamycin when mixed with the diluent is in the range 0.25 mg/ml to 2 mg/ml.

15. A product containing a concentrate solution of rapamycin and a diluent, as a combined preparation for mixing prior to IV injection to give a solution free of non-ionic surfactant and having a concentration of rapamycin in the range 0.1 mg/ml to 4 mg/ml; said concentrate solution consisting essentially of rapamycin in propylene glycol in the range 0.5 mg/ml to 4 mg/ml; said diluent consisting essentially of water, the ratio of concentrate to diluent being in the range from 40:60 to 75:25 volume percent.

* * * * *